United States Patent [19]

Cherniak

[11] Patent Number: 4,819,644
[45] Date of Patent: Apr. 11, 1989

[54] BASE PLATE TO FORM AN INSOLE FOR AN ORTHOTIC FOOT BRACE AND A METHOD OF FORMING AN ORTHOTIC FOOT BRACE

[76] Inventor: Jaime G. Cherniak, Ave. Tiradentes No. 10, Centro, Commercial Dayln, Ens. Naco, Santo Domingo, Dominican Republic

[21] Appl. No.: 114,036

[22] Filed: Oct. 29, 1987

[51] Int. Cl.⁴ ............................................... A61F 5/14
[52] U.S. Cl. ..................................... 128/596; 33/5; 33/6; 36/43; 128/603; 128/615
[58] Field of Search ............... 128/596, 603, 615, 581; 36/43; 33/3 R, 3 A, 3 B, 3 C, 4, 5, 6

[56] References Cited

U.S. PATENT DOCUMENTS

| | | | |
|---|---|---|---|
| 1,264,670 | 4/1918 | McMaster | 33/6 |
| 1,953,684 | 4/1934 | McMaster | 33/6 |
| 4,387,516 | 6/1983 | Laux | 33/3 R X |
| 4,603,698 | 8/1986 | Cherniak | 128/615 X |
| 4,677,766 | 7/1987 | Gudas | 36/43 |

Primary Examiner—Edgar S. Burr
Assistant Examiner—Moshe I. Cohen
Attorney, Agent, or Firm—McAulay, Fields, Fisher, Goldstein & Nissen

[57] ABSTRACT

The present invention provides a base plate that forms an insole for an orthotic foot brace. The base plate has a graph inscribed on one of its surfaces. It includes first and second coordinate markings to define positions for attaching podiatric appliances to the base plate. The foot of the patient can be placed against the base plate on the graph and a traced outline can be formed of the foot. After attachment of the podiatric appliance at positions defined by the coordinates and prescribed by a health care provider, the base plate can be cut to the outline of the foot to form the insole of the orthotic foot brace.

8 Claims, 7 Drawing Sheets

BASE PLATE TO FORM AN INSOLE FOR AN ORTHOTIC FOOT BRACE AND A METHOD OF FORMING AN ORTHOTIC FOOT BRACE

BACKGROUND OF INVENTION

Orthotic foot braces, worn within the shoe, are utilized by podiatrists and related health care providers for post operative and corrective treatment of the foot. Such orthotic foot braces include podiatric appliances that independently attach to therapeutic insoles. This arrangement of insole and podiatric appliance is advantageous and cost effective in that it obviates the necessity of custom made orthopedic shoes.

Conventionally, the podiatrist or other health care provider indicates the name of each of the appliances to be used, its measurements, and an insole size or number on each prescription given to the patient. The associated prescribed insole and appliances are then purchased by the patient at a drug store or dealership. U.S. Pat. No. 4,603,698, issued to Jaime Guttman Cherniak (the inventor herein) on Aug. 4, 1986, provides a system in which podiatric appliances are securable to an insole by provision of small U shaped wires. The insole of Cherniak is provided with a tangible grid of hole-like mounting sites, extending in a uniform, predetermined pattern. The insoles, which come in a range of sizes, can have applied indicia, contrasting coloration or can be utilized with a graph paper template in the nature of a prescription, so that each of the mounting sites can be assigned a unique address. The purpose of this is to allow the podiatric appliance to be attached to mounting sites that are prescribed by the health care provider. A problem arises, even in the system described in the Cherniak patent, in that the outline of an injured or malformed foot can lie between insole sizes. As such, it is sometimes impossible for the health care provider to prescribe an insole to fit the patient. Moreover, since a malformed foot can deform a shoe, even when an appropriate base plate size can be selected, the selected insole can be too large to fit within the shoe in the first instance. In order to alleviate the problems associated with insoles incorporating attachable podiatric appliances, the present invention provides an insole formed from a base plate that can be cut to the outline of the foot. The base plate has an inscribed graph on one of its surfaces. The podiatrist can use the coordinates of the graph to easily prescribe to the patient the proper placement of the podiatric appliance. Since the podiatrist appliances must often be moved after an initial wearing period, the podiatrist can convey the change of the location of the podiatric appliance by simply conveying to the patient the coordinates for the reinstallation of the podiatric appliance. An additional advantage of the base plate of the present invention is that, since the base plate is cut to the exact size of the foot, individual base plates do not have to be manufactured and prescribed.

SUMMARY OF THE INVENTION

In one of its aspects, the present invention provides a base plate to form an insole for independently attachable podiatric appliances that are applied to a patient's foot under the direction of a health care provider. The base plate comprises a stiffly flexible, yet shearable, rectangular, planner sheet having a thickness, a pair of opposed, parallel surfaces separated by the thickness, and a graph inscribed on one of the surfaces. The graph has at least one pair of orthogonal axes. Means are provided for indicating the coordinates, relative to the axes, of the positions for attaching the podiatric appliances to the sheet. The means include at least one set of spaced, first coordinate markings, located along one of the axes and at least one set of spaced, second coordinate markings, located along the other of the axes. The first and second coordinate markings define the coordinates of the positions. As a result of the aforementioned invention, a patient can place his or her foot on the base plate, within the bounds of the graph and form a traced outline of the foot on the graph by a marking device. The patient can then attach the podiatric appliances to the base plate at positions prescribed to the patient by the health care provider, by the first and second coordinate markings. Thereafter, the patient can cut the sheet to the outline of the foot to form an insole.

In another of its aspects, the present invention provides a method of forming an orthotic foot brace for therapeutic treatment of the foot of a patient under the care of a health care provider. This method includes providing a base plate, as described above, and at least one podiatric appliance having a basewall member that is operable to be brought into an abutting, overlying relationship to the graph of the base plate. Means, associated with the base plate and the basewall member, are provided for securing the podiatric appliance, at its basewall member to the sheet in an abutting, overlying relationship to the graph. The foot is placed against the one surface, within the boundaries of the graph. A traced outline of the foot is formed on the graph with a marking device. The basewall member of the podiatric appliance is then attached, by the securement means, to the base plate at a position prescribed by the health care provider to the patient by the first and second coordinate markings. Thereafter, the base plate can be cut to the traced outline of the foot to form the insole of the orthotic foot brace.

DETAILED DESCRIPTION

Figure 1:
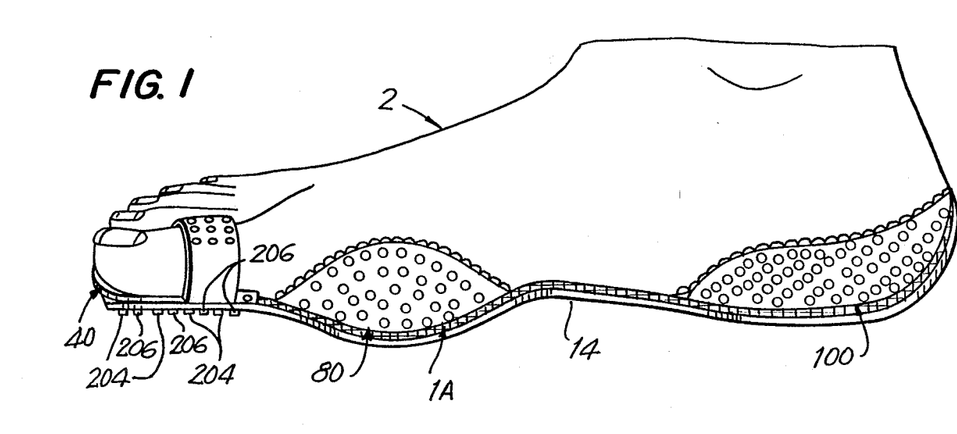
FIG. 1 is a left side perspective view of an orthotic foot brace of the present invention installed on the foot of a patient.
Figure 2:
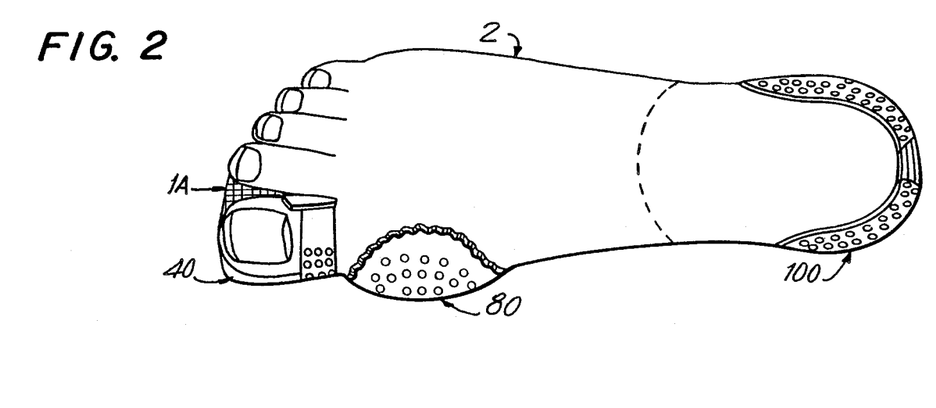
FIG. 2 is a top plan view of FIG. 2.
Figure 4:
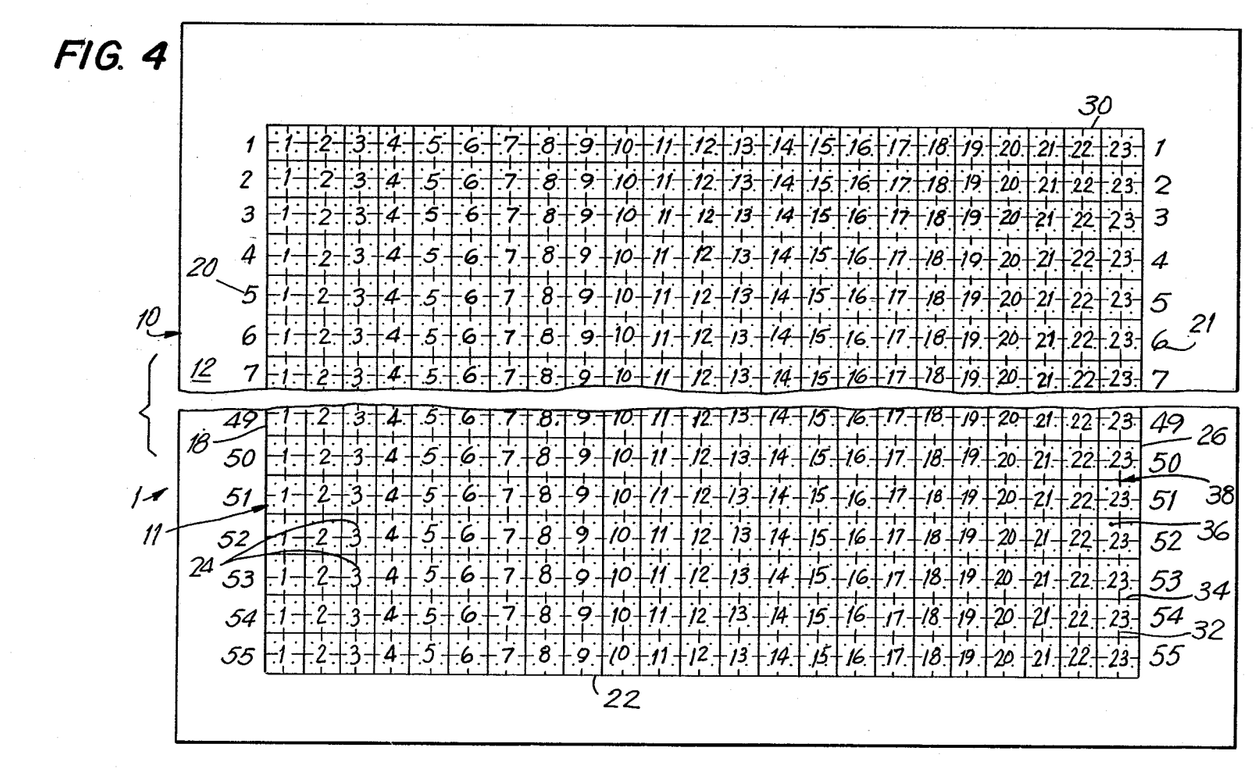
FIG. 4 is a top plan view of the Base Plate of the present invention.

Referring to FIGS. 1, 2 and 4, podiatric appliances of the present invention, such as a toe splint appliance 40, a bunion support appliance 80, and a heel support appliance 100 are attached to an insole 1A cut from the base plate 1 of the present invention to form an orthotic foot brace worn on a foot 2. Base plate 1 is a stiffly flexible, yet shearable, rectangular, planar sheet 10. Inscribed on surface 12 of the planar sheet 10 is a graph 11 having a set of two pairs of orthogonal axes 18, 22 and 26, 30. A network of lines 32 and 34 form a plurality of squares, as indicated at 38. Within each of these squares is a mounting site, as indicated by 36, which in the illustrated prefered embodiment, comprises a hole through the sheet 12. The aforementioned podiatric appliances such as illustrated at 40, 80, and 100 are preferably attached to the base plate 1 through the hole of the mounting sites, as indicated at 36, by U shaped wires 200, the ends of which (204 and 206) are inserted through holes forming the mounting sites 36, and then crimped. The patient at the direction of the health care provider places his or her foot on the planar sheet 10 within the bounds of the graph 11 and traces the outline with a marking device. The podiatric appliances such as illustrated by 40, 80, or 100 are then attached to the sheet 1 at positions of the graph 11, defined by first and second coordinate markings 20 and 24, prescribed by the podiatrist or other health care provider. For instance, toe splint appliance 40 would be attached at a position defined by first and second coordinate markings (3.5, 8), (3.5, 11), (12, 8), and (12, 11). These coordinate markings can either be the general outline of the appliance or the squares containing the mounting sites through which the wire ends 204 and 206 are inserted.

Figure 3:
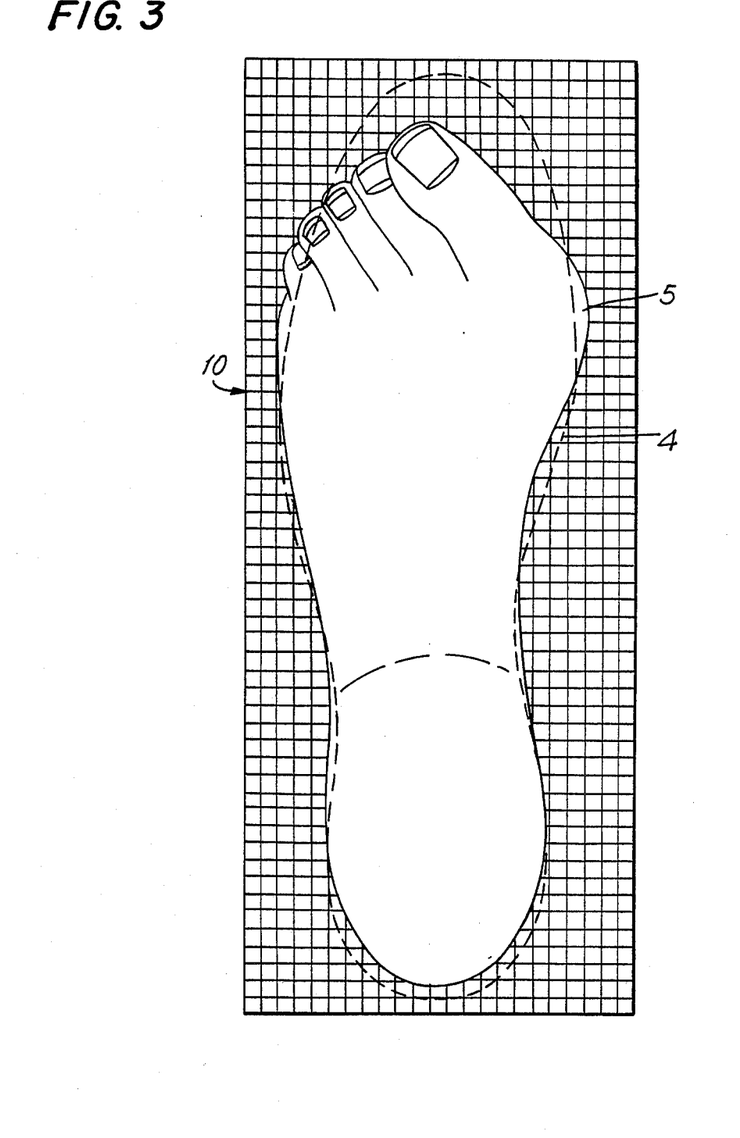
FIG. 3 is a top plan view comparing the outline of a malformed foot with a prescribed insole (shown in broken lines) overlying an imprinted graph of the subject invention.

FIG. 3 illustrates the difficulty of prescribing an insole to fit a malformed foot 5. An appropriate insole size to fit the shoe is indicated by the broken lines 4. As can be seen, such an insole size 4 does not fit the foot 5. If the next insole size is tried, while perhaps it would fit the foot 5, it would not fit within the shoe of the patient.

Graph 11 is inscribed on the surface 12 of sheet 10. Graph 11 preferably has a set of two pairs of orthogonal axes 18, 22 and 26, 30, connected end to end to form an inscribed rectangle within the sheet 10. The rectangle thus has opposite, parallel lengthwise sides 18 and 26; and opposite, parallel transverse sides 22 and 30. Sets of identical first coordinate markings, as indicated by 20 and 21, are preferably, respectively provided along axes 18 and 26. The markings indicated by 20 and 21, are preferably numerical and comprise a set of integers, 1 through 55, inclusive. As illustrated, each one of the markings of one set, as indicated by 20, are located directly opposite to an identical marking of the other set, as indicated by 21. Identical sets of second coordinate markings, as indicated by 24, are located between identical first coordinate markings of sets 20 and 21. Each one of the second coordinate markings of sets 24 are located opposite to an identical second coordinate marking of another of the sets 24. As can be appreciated, the purpose of these identical sets of markings is to permit a patient to easily locate the coordinate position on graph 11 for attaching podiatric appliances. In this regard, to further aid the patient, a network of lines can also be provided. This network of lines includes a first plurality of parallel, spaced lines 32 and an intersecting second plurality of lines 34. Lines, 32, extend, between the axes 22 and 30, forming the transverse sides of the inscribed rectangle, in a parallel orientation to the axes 18 and 26. Lines, as indicated by 34, extend between axes 18 and 26 forming the lengthwise sides of the inscribed rectangle in a parallel orientation to axes 22 and 30. The network of lines, as indicated by 31 and 32, intersect one another at right angles.

The spacing between adjacent lines 32 and the spacing between adjacent lines 34 are equal to thereby form a plurality of squares, as indicated by 38, from the intersection of lines 32 and 34. Each of the second coordinate markings of a set 24 is located at an intersection of a line of the first plurality 32 and a line of the second plurality 34. As will be described in greater detail hereinafter, a tangible grid of mounting sites is provided, such as indicated by 36, to mount the orthopedic appliances of the present invention. Each of these mounting sites, as indicated by 36, are centrally located within each of the squares, as indicated by 38. The spacing between adjacent lines of the sets 32 and 34 and thus, the mounting sites, as indicated by 36 is preferably 3 millimeters. Additionally, in preferred embodiment, the spacing between adjacent first coordinate markings and second coordinate markings is two lines, and hence, six millimeters.

The graph 11 of the subject invention provides the set of lines 32 and 34, the two sets of axes 18, 22 and 26, 30, and the sets of markings 21 and 24 to enable the patient to easily locate a position of podiatric appliance attachment. It is understood however that the present invention comprehends any orthogonal axes graphic system. Although not preferred, an embodiment of the present invention could be constructed with or without mounting sites 36 and with only one set of orthogonal axes 18 and 22, one set of first coordinate markings located along axes 18 and one set of second coordinate markings located along axes 22.

The present invention calls for the graph 11 to be inscribed on at least one of the surfaces, 12 of the planner sheet 10. It is understood that a graph such as 11 could also be inscribed on the reverse opposite surface 14 of the planner sheet 10.

Figure 5:
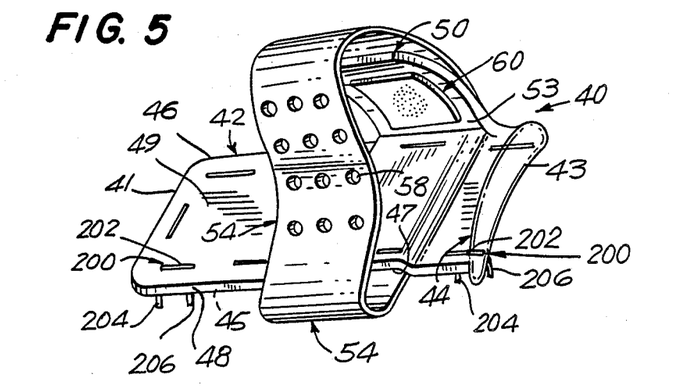
FIG. 5 is a left side, perspective view of the Toe Splint Appliance of the present invention.
Figure 6:
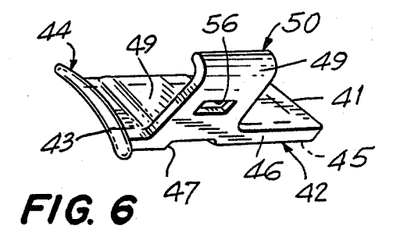
FIG. 6 is a right side perspective view of the Toe Splint Appliance illustrated in FIG. 3 with a Bandage Member of the present invention removed.
Figure 7:
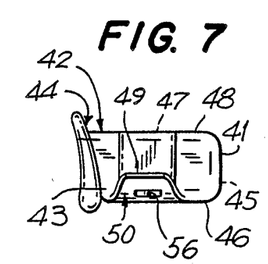
FIG. 7 is a top plan view of FIG. 6.

Referring now to FIG. 5, a Toe Splint Appliance 40 of the present invention is illustrated. The Toe Splint Appliance 40 is particularly useful after nail removal surgery and to generally stablize the toe to prevent unwanted movement thereof. It is also useful, in conjunction with the other illustrated appliances, in the treatment of Hallox Valgus by application of a corrective force over a period of time and thus, correct deformed fleshy tissue and joint capsules toward normal. Referring also to FIGS. 6 and 7, the toe splint appliance 40 of the present invention includes a basewall member 42, a vertically upstanding, curved member 50, a bandage member 54 and an attachment tab member 60. Basewall member 42 has a rectangular, planar configuration, sized to fit beneath toe of the patient. Basewall member 42 has a pair of opposed ends 41 and 43 spaced apart from one another, a pair of opposed lengthwise edges 46 and 48, spaced apart from one another, connecting ends 41 and 43. A lip element 44 is preferably formed at end 43 of the basewall member 42. Lip element 44 is sized to fit under the base of the toe of the patient in order to provide support for the overlying toe joint and to prevent outward movement of the entire splint appliance 40. A bottom surface 45 of basewall member 42 is preferably provided with a transverse recess 47 spaced from end 43. Vertically upstanding, curved member 50 is formed on one of the lengthwise edges 46 of the basewall member 42 at recess 47 and curves over a top surface 49 of basewall member 42. The width of the curved basewall member 50 is at least equal to the width of the recess 47.

Figure 8:
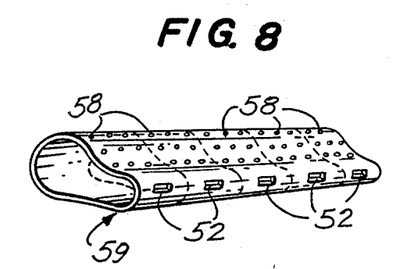
FIG. 8 is a perspective view of stock material utilized in forming the Bandage Member of the present invention.
Figure 9:
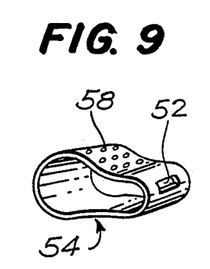
FIG. 9 is a perspective view of the Bandage Member of the present invention.

Bandage member 54 is illustrated in FIGS. 8 and 9. Bandage member 54 is of tubular configuration, having a length sized to fit within recess 47 and an inner diameter sized such that when the basewall member 42 and the curved member 50 are inserted through the inner diameter of bandage member 54, with bandage member 54 extending through recess 47, the toe of the patient is operable to extend through the inner diameter with the bandage member 54 closely fitting around the toe.

Bandage member 54 and curved member 50 are provided with a pair of rectangular slots 52 and 56, respectively located so as to be operable to be brought into alignment with one another when bandage member 54 encircles the curved member 50. Bandage member 54 is also preferably provided with an array of openings, as indicated by 58, spaced from slot 56, such that when slot 56 is brought into alignment with slot 52, openings 58 overlie the toe. The purpose of openings 58 is for ventilation and for medication of the toe when the toe splint appliance 40 is installed. Openings 58 can be omitted.

With reference to FIG. 8, bandage member 54 can be supplied in stock form as a long tube 59 having spaced slots 52 and arrays of openings 58 along its length. Bandage member 54 can then be cut from such tube and then placed on the toe splint appliance 40 when necessary.

Figure 10:
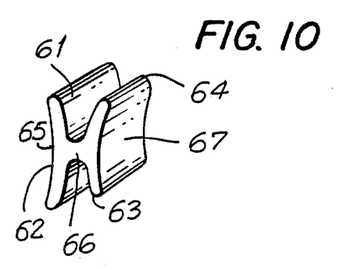
FIG. 10 is a left side, perspective view of an Attachment Tab Member utilized in the Toe Splint Appliance illustrated in FIG. 5.
Figure 11:
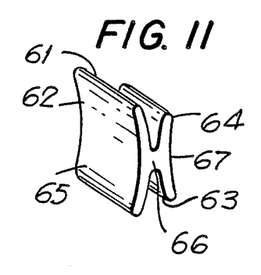
FIG. 11 is a right side, perspective view of an Attachment Tab Member utilized in the Toe Splint Appliance of FIG. 5.
Figure 14:
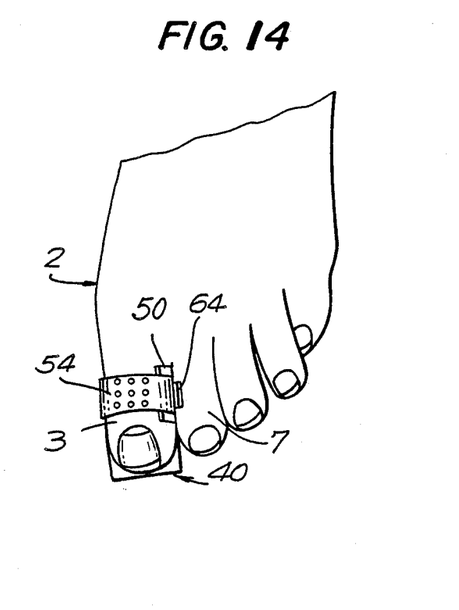
FIG. 14 is a fragmentary, plan view of the Toe Splint Appliance illustrated in FIG. 5 installed on a toe.

Attachment tab member 60 is illustrated in FIGS. 10 and 11. Attachment of the bandage member 54 is preferably effectuated by the illustrated attachment tab member 60. Attachment tab member 60 has an 'I' beam-like transverse crossection, a pair of opposed flange elements 62 and 64 spaced apart from one another and a web element 66, centrally located between the flange elements 62 and 64, connecting flange elements 62 and 64 to one another. The flange elements 62 and 64 are flexible and have an outwardly curving, planar configuration. Flange elements 62 and 64 also have a pair of opposite inner surfaces, 61 and 63, facing one another, and a pair of opposite, outer surfaces, 65 and 67, facing away from one another. The radius of curvature of the inner surface 61 is preferably equal to the radius of curvature of the interior surface 53 (FIG. 5) of the curved member 50, so that when the attachment tab member 60 is installed, inner surface 61 lies flush against the interior surface 53 of the curved member 50. After the Bandage Member 54 is placed on basewall member 42 and curved member 50, attachment tab member 60 is inserted through slot 52 (flange 64 first) of curved member 50 and through the aligned slot 42 to the bandage member 54. The bandage member 54 is thus secured by the pressure of the flange elements 62 and 64. With reference also to FIG. 14, the illustrated flange element 64 preferably has a size and a selected curvature that is substantially equal to an adjacent toe 7. The purpose of this is to provide a toe separater by the attachment tab member 60.

Figure 12:
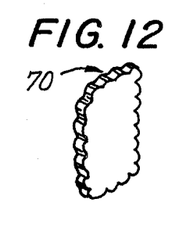
FIG. 12 is a front perspective view of a Square-shaped Cushioning Member utilized with the Attachment Tab Member illustrated in FIGS. 10 and 11.
Figure 13:
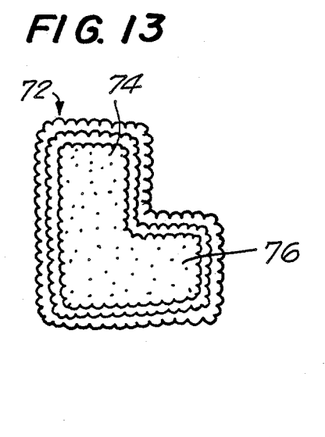
FIG. 13 is a top plan view of an L-Shaped Cushioning Member utilized with the Toe Splint Appliance illustrated in FIG. 5.

Referring now to FIGS. 12 and 13, square-shaped, cushioning members, such as illustrated by square-shaped, cushioning member 70 of FIG. 12 can be attached to the outer surfaces 65 and 67 of the attachment tab member 60. The square-shaped, cushioning member 70 is fabricated from a self-adhering cushioning material, well known in the art. Referring to FIG. 13, an L-shaped cushioning member 72 can be installed along the top surface 49 of basewall member 42 and the interior surface 53 of curved member 50.

Figure 15:
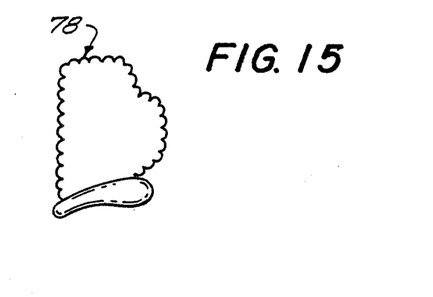
FIG. 15 is a top plan view of a sock-like elastic Bandage Member of the present invention.

L-shaped cushioning member 72 has a pair of intersecting arms 74 and 76 that are mutually perpendicular to one another. Arm 74 has a length and width equal to that of the basewall member 42. Arm 76 has a length and width equal to length and width of interior surface 53 of the curved member 50. L-shaped cushioning member 72 is installed on the toe splint appliance 40 with Arm 74 attached to basewall member 42 and with arm 76 attached to the interior surface 53 of curved member 50. In this regard L-shaped cushioning member 72 can preferably be fabricated from a self-adhering, felt-like material, well known in the art. Referring to FIG. 15, a sock-like elastic bandage 78 can be used to cover the toe and the toe splint appliance 40. It is understood that the cushion provided by the cushioning members 70 and 72 could be provided by tape and cotton wadding, or directly integrated into the components of toe splint appliance by plastic foam construction.

Figure 16:
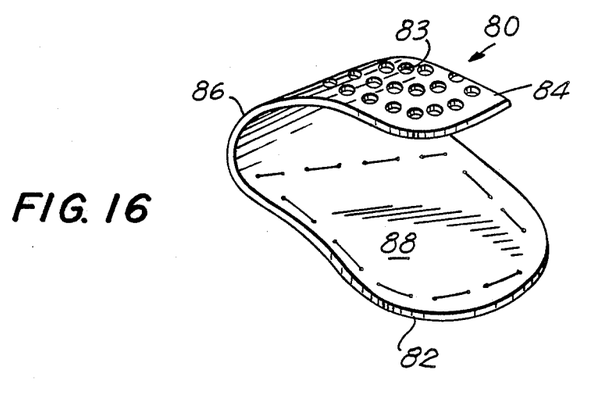
FIG. 16 is a perspective view of a Bunion Support Appliance of the present invention.
Figure 17:
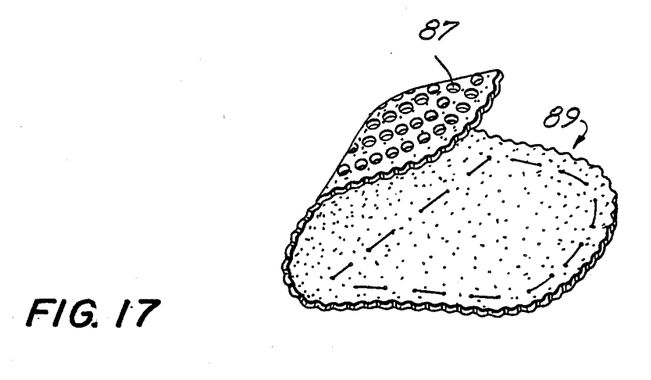
FIG. 17 is a perspective view of a Bunion Support Cushioning Member utilized with the Bunion Support Appliance illustrated in FIG. 16.

The Bunion Support Appliance 80 of the present invention is illustrated in FIG. 16. Bunion Support Appliance 80 is used to relieve pressure on the bunion after surgery and to prevent the bunion from rubbing against the interior of the shoe. Bunion Support Appliance 80 has a saddle-like configuration that includes at flat planar base portion 82, a curved, planar upper supporting portion 84 overlying the base portion 82 and vertically spaced from the base portion 82. Also included, is a curved, planar lateral supporting portion 86, located between portions 84 and 82. Lateral supporting portion 86 connects base portion 82 with upper supporting portion 84 with base portion 82 and upper covering portion 84 extending from lateral supporting portion 86. Appliance 80 has an interior surface 88 formed by the interior surfaces of upper supporting portion 84 extending from lateral portion 86 and base portion 82. Interior surface 88 is configured to closely conform to the exterior surface of the foot located at the medial side of the first metararsophalangeal joint. Bunion Support Appliance 80 is preferably provided with a plurality of openings 83 to allow for ventilation of the foot and to allow for medication of the foot when bunion support appliance 80 is in use. Openings 83 are optionally included. Bunion support appliance 80 can also be preferably provided with a bunion support cushioning member 89, illustrated in FIG. 17. Bunion support cushioning member 89 is configured to lie flush against interior surface 88 of the bunion support appliance 80. Bunion support cushioning member 89 can also be provided with a plurality of optional openings 87 that align with the openings 83 when cushioning member 89 is inserted within interior surface 88 of bunion support appliance 80.

Figure 18:
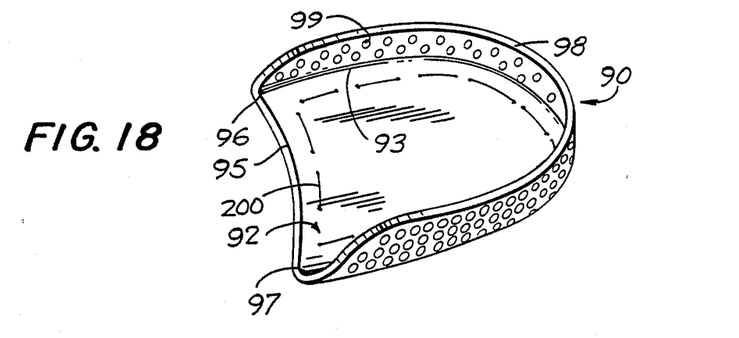
FIG. 18 is a perspective view of a Heel Support Appliance of the present invention.
Figure 19:
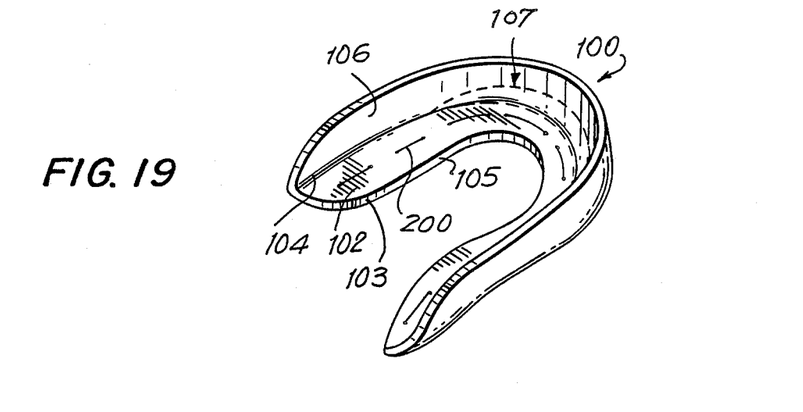
FIG. 19 is a perspective view of an alternative embodiment of a Heel Support Appliance of the present invention.
Figure 20:
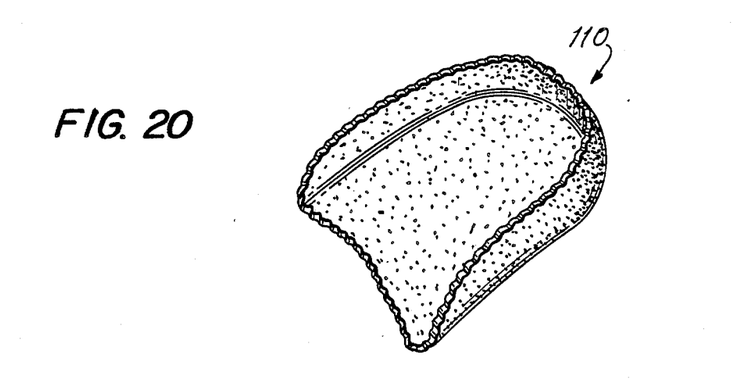
FIG. 20 is a perspective view of a Heel Support Cushioning Member utilized with the Heel Support Appliance illustrated in FIG. 18.

FIG. 18 illustrates heel support appliance 90 of the present invention. The heel support appliance 90 comprises a basewall member 92 and an upstanding, lateral sidewall member 98. Basewall member 92 has a rear edge 93, having ends 96 and 97, and a front edge 95 connecting the ends 96 and 97. Vertically, upstanding sidewall 98 preferably formed at the rear edge 93 and extends from end 96 to end 97 of the rear edge 93. With reference now to FIG. 19, an alternative embodiment 100 of a heel support appliance of the present invention is illustrated. Heel support appliance 100 includes a horse shoe-like basewall 102 having an inner arcuate edge 103 and an outer arcuate edge 104 spaced from inner arcuate edge 103. A vertically upstanding sidewall 106 is formed at the outer edge 104 and extends along the outer edge of 104. As illustrated, different types of orthotic devices such as heel wedges (shown by broken lines as 107) and the like could be utilized with embodiments 90 and 100 connected to basewall members 92 and 102. Referring again to the heel support appliance 90, illustrated in FIG. 18, the sidewall 98 can be provided with openings, such as illustrated by 99 to permit ventilation of the foot. As can be appreciated, the sidewall 106 of alternative embodiment 100 could similarly be provided with openings. These openings, such as illustrated 99 are optional. FIG. 20 illustrates a Heel Support Cushioning Member 110 to be preferably utilized with the Heel Support Appliances 90 and 100. Heel Support Cushioning Member 110 is configured to closely fit on the basewalls 92 and 102 and within the sidewalls 98 and 106. Heel support cushioning member 110 can be fabricated from a self-adhering, felt-like material known well in the art. Both of the embodiments for the heel support appliance 90 and 100 of the present invention are operable to perform the function of stabilizing the heel of the foot relative to the toes when the toe splint appliance 40 is utilized. The heel support appliances 90 and 100 can also be used without the toe support appliance 40 and the bunion support appliance 80 for such theraputic functions as positively affecting the posture of the patient. Likewise, the toe support appliance 40 of the present invention can be utilized alone for stabilizing and protecting the toe of the patient after nail removal surgery. Similarly, bunion support appliance 80 can be used alone to relieve pressure and pain in the foot caused by bunions. Referring again to FIGS. 1 and 2, all the appliances 40, 80 and 90 or 100 of the present invention are utilized with the formed insole 1A of the present invention to treat Hallux Valgus. As illustrated in FIGS. 1 and 2 the toe support appliance 40 is applying pressure to correct the orientation of the major toe of the foot. The heel support appliance 100 is holding the heel of the foot relative to the toe so that the entire foot does not turn during treatment. The bunion support appliance 80 is providing lateral support for the foot, thus urging the great toe in the orientation of the toe splint appliance 40.

The pediatric appliances 40, 80, 90 and 100 are preferably secured to base plate 1 by means of U-shaped wires 200, round in transverse crossection. Each of the U-shaped wires 200 is embedded in mounting base or basewall member of the podiatric appliance to be secured. In this regard, the basewall member of the bunion support appliance 80 is the base portion 82 thereof. For exemplary purposes, referring to FIG. 5, toe splint appliance 40 has a plurality of the U-shaped wires 200, having the central portions 202 embedded in basewall member 42. Each of the wires 200 has a pair of end portions 204 and 206 protruding from basewall member 42 in a downwardly depending direction. With reference to FIG. 4, each of the mounting sites, such as illustrated 36, can comprise holes communicating between the surfaces 12 and 14 of the sheet 10. The end portions 204 and 206 are spaced, so that when the basewall member 42 is placed in an abutting relationship with the surface 12 of the planar sheet 10, the end portions 204 and 206 are operable to extend through the mounting sites, such as illustrated 36, and emerge from the opposite surface 14 of the planar sheet. The emergent ends of the protruding end portions 204 and 206 can then be crimped towards one another to secure the podiatric appliance, such as toe splint appliance 40 to base plate 1.

The present invention also includes attaching the podiatric appliances by other methods such as glues and the like. Therefore, an embodiment of the present invention could be made without the U-shaped wires 200 and the mounting sites as indicated by 36. Such an embodiment is not preferred in that it would require another separate component, to wit; the glue, for the patient to purchase and use.

The base plate 1 of the present invention is preferably fabricated from plastics utilizing well-known plastic forming techniques. The podiatric appliances 40, 80, 90 and 100 can similarly be fabricated from plastics. It is preferred that the outer surfaces of the bunion support appliance 80 and the heel support appliances 90 and 100 be covered with foam rubber to cushion the foot and to prevent damage to the shoe. It is, of course, possible to form base plate 1 and the appliances 40, 80, 90 and 100 from metal. As can be appreciated, fabrication from metal is not preferred because of cost considerations.

While specific embodiments of the invention have been shown the invention should not be considered as so limited, but is limited only as set forth in the claims.

I claim:

1. A base plate to form an insole for independently attachable podiatric appliances that are applied to a patient's foot under the direction of a health care provider, said base plate comprising a stiffly flexible, yet shearable, rectangular, planar sheet including,
   a thickness,
   a pair of opposed, parallel surfaces separated by said thickness,
   a graph inscribed on one of said surfaces, said graph having,
      at least one pair of orthogonal axes, and
      means for indicating the coordinates, relative to the axes, of positions for attaching such podiatric appliances to said sheet, said means includiing,
      at least one set of spaced, first coordinate markings, located along one of the said axes, and
      at least one set of spaced, second coordinate markings, located along the other of the said axes, said first and second coordinate markings defining said coordinates of said positions, whereby said patient can place his or her foot on said base plate, within the bounds of the said graph, and form a traced outline of the said foot on said graph by a marking device, attach the said podiatric appliances to the said base plate at positions prescribed by said health care provider to said patient by said first and said second coordinate markings and thereafter cut the said sheet to the said traced outline to form said insole, and a plurality of mounting holes located at said positions.

2. The base plate of claim 1 wherein:

said graph has a set of two pairs of orthogonal axes connected end to end to form an inscribed rectangle within the said sheet having opposite parallel lengthwise sides and opposite, parallel transverse sides, a pair of identical sets of said spaced first coordinate markings, located along said axes forming said lengthwise sides, with said lengthwise sides being located between said sets of said first coordinate markings and with each one of said first coordinate markings of a said set being located opposite to an identical said first coordinate marking of a said other set, and a plurality of identical sets of said second coordinate markings, each set of which is located between a pair of opposite identical, said first coordinate markings, with each one of said second coordinate markings of one of said sets being located opposite to an identical said second coordinate marking of another of the said sets.

3. The base plate of claim 2 wherein said graph further includes:

a first plurality of parallel, spaced lines, extending between said axes forming said transverse sides of said inscribed rectangle in a parallel orientation to the said axes forming the said lengthwise sides of the said inscribed rectangle, and a second plurality of parallel, spaced lines, extending between said axes forming the said lengthwise sides of the said inscribed rectangle in a parallel orientation to the said axes forming the said transverse sides of the said inscribed rectangle, said second plurality of lines intersecting said first plurality of lines to form a network of lines within the said inscribed rectangle.

4. The base plate of claim 3 wherein:

the spacing between said lines of said first plurality of lines and the spacing between said lines of the second plurality of lines are equal to form a plurality of squares from said formed network of said lines; and each of said second coordinate markings is located at an intersection of a said line of said first plurality of lines with a said line of said second plurality of lines.

5. The base plate of claim 4 wherein:

each of said sets of first coordinate markings comprise a set of integers of 1 through 55 inclusive;

each of said sets of second coordinate markings comprise a set of integers of 1 through 23 inclusive;

said first coordinate markings are spaced apart from one another such that the scale of increase between adjacent first coordinate markings is two lines of said second plurality of lines; and said second coordinate markings are spaced apart from one another such that the scale of increase between adjacent second coordinate markings is two lines of said first plurality of lines.

6. The base plate of claim 5 wherein:

the spacing between adjacent lines is 3 millimeters.

7. The base plate of claim 6 wherein:

each of said holes being centrally located within a said square of the said plurality of squares to form an attachment site for said podiatric appliance using embedded U-shaped wires to attach said podiatric appliance to said base plate.

8. A method of forming an orthotic foot brace for therapeutic treatment of the foot of a patient under the care of a health care provider, including:

providing a base plate including a stiffly flexible, yet shearable, rectangular planar sheet having, a thickness, a pair of opposed parallel surfaces separated by said thickness, and a graph inscribed on one of said surfaces, said graph having at least one pair of orthogonal axes, and means for indicating the coordinates, relative to the said axes, of positions for attaching said podiatric appliances, said means including, at least one set of spaced, first coordinate markings, located along one of the said axes, and, at least one set of spaced, second coordinate markings, located along the other of the said axes, said first and said second coordinate markings defining said positions;

providing at least one podiatric appliance having a basewall member opposite to and brought into and abutting, overlying relationship to the said graph;

providing means, associated with said base plate and said basewall member, for securing said podiatric appliance at its said basewall member to the said sheet in an abutting overlying relationship to the said graph;

placing said foot against said one surface, within the boundaries of the said graph;

forming a traced outline of the said foot on said graph with a marking device;

attaching said basewall member of said podiatric appliance, by said securement means, to said sheet at a said position prescribed by said health care provider to said patient by said first coordinate markings and said second coordinate markings, and, cutting said sheet to the said traced outline of the said foot to form said orthotic foot brace.

* * * * *